(12) United States Patent
Caldiero

(10) Patent No.: US 9,149,346 B1
(45) Date of Patent: Oct. 6, 2015

(54) METHOD FOR SYNTHETIC POLYMER TOOTH REPLACEMENT

(71) Applicant: Kelly Walter Lee Caldiero, Altadena, CA (US)

(72) Inventor: Kelly Walter Lee Caldiero, Altadena, CA (US)

(*) Notice: Subject to any disclaimer, the term of this patent is extended or adjusted under 35 U.S.C. 154(b) by 0 days.

(21) Appl. No.: 14/588,725

(22) Filed: Jan. 2, 2015

Related U.S. Application Data

(60) Provisional application No. 62/065,425, filed on Oct. 17, 2014.

(51) Int. Cl.
- *A61C 5/00* (2006.01)
- *A61C 8/00* (2006.01)
- *A61L 27/00* (2006.01)
- *A61K 45/06* (2006.01)
- *A61B 17/16* (2006.01)
- *C08L 23/12* (2006.01)
- *C08L 63/00* (2006.01)

(52) U.S. Cl.
CPC .............. *A61C 8/0016* (2013.01); *C08L 23/12* (2013.01); *C08L 63/00* (2013.01)

(58) Field of Classification Search
None
See application file for complete search history.

(56) References Cited

U.S. PATENT DOCUMENTS

| | | | | |
|---|---|---|---|---|
| 2005/0142163 A1* | 6/2005 | Hunter et al. | | 424/423 |
| 2009/0124607 A1* | 5/2009 | Bladh et al. | | 514/220 |

OTHER PUBLICATIONS

U.S. Appl. No. 14/588,725 Scifinder Search.*

* cited by examiner

*Primary Examiner* — James J Seidleck
*Assistant Examiner* — Peter A Salamon
(74) *Attorney, Agent, or Firm* — Barry Choobin; Patent 360

(57) ABSTRACT

The present invention discloses a synthetic polymer tooth replacement for replacing a missing tooth. The synthetic tooth replacement is a periodontic implant suitable for natural and reconstructed periodontic in the geometric/topographic construct similar to that of a natural tooth's dentin below the gumline. The synthetic polymer tooth replacement is made of a composition comprising a moldable resin and weighted particular additives. The replacement is formed by centrifuging the composition and pouring into a mold. The mold is customized to the recipients missing tooth, resulting in a replacement that has an exterior that is configured to bow out over a period of time, such that when the partially cured replacement is placed in a recipient's dental cavity, the replacement locks into the place while fully curing over a period of time. The advantages are the natural feel and non-invasive nature of the polymer dentin, which does not disturb the natural state of the dentin cavities. The synthetic polymer tooth replacement allows for replacement teeth without the need for bone grafting.

3 Claims, 4 Drawing Sheets

METHOD FOR SYNTHETIC POLYMER TOOTH REPLACEMENT

CROSS-REFERENCE TO RELATED APPLICATIONS

This application claims the priority of U.S. Provisional Patent Application No. 62/065,425, filed on Oct. 17, 2014, with the tile, "Synthetic Polymer Tooth Replacement", and the content of which is incorporated herein by reference in its entirely.

BACKGROUND

1. Technical Field

The embodiments herein generally relate to the field of dentistry and dental health. The embodiment herein particularly relate to the field of dental restorations, implants and prosthesis. The embodiments herein more particularly relate to the dental implant profiles similar to those of a natural tooth and its surrounding gingiva. The embodiments also relate to the dental implant, which creates a substantially improved fit between the implant and the tooth restoration analogue. The embodiment further relates to the dental implant, which fits and improves both cosmetic appearance and functional utilization.

2. Description of the Related Art

Human teeth are the small, calcified hard, whitish structures found in the human mouth. The function of teeth is mechanically breaking down food by cutting and crushing them in preparation for swallowing and digestion. The roots of teeth are embedded in the maxilla (upper jaw) or the mandible (lower jaw) and are covered by gums. Teeth are made of multiple tissues of varying density and hardness.

The tooth disorders or dental pathology is any condition of the teeth that is congenital or acquired. The most common dental disorders are dental caries, dental caries, dental abscess, dental injuries etc. These disorder or injuries cause the dental tissue damage. The disorders or injuries are treated or rectified by surgery or artificial dental implants.

A dental implant is a surgical component that interfaces with the bone of the jaw or skull to support a dental prosthetics such as a crown, bridge, denture, and facial prosthesis or to act as an orthodontic anchor.

The basis for modern dental implant is a biological process called Osseo integration where materials such as titanium, form an intimate bond to bone. The implant fixture is first placed so that it is likely to Osseo integrate, and then a dental prosthetic is added. A varied amount of healing time is required for Osseo integration before the dental prosthetic such as tooth, bridge or denture are attached to the implant or an abutement is placed which holds a dental prosthetic's.

The success or failure of implants depends on the health of the person receiving it, drugs which impact the chances of Osseo integration and the health of the tissues in the mouth. The amount of stress that will be put on the implant and fixture during normal function is also evaluated. Planning the position and numbers of implants is key to the long-term health of the prosthetic since biomechanical forces created during chewing can be significant. The position of implants is determined by the position and angle of adjacent teeth, lab simulation or by using computer tomography with CAD/Cam simulations and surgical guide called stents. The prerequisites to long-term success of Osseo integrated dental implants are healthy bones and gingiva. Since there are chances of atrophy after tooth extraction pre-prosthetic procedures such as sinus lifts or gingival grafts are sometimes required to create ideal bone and gingiva.

The final prosthetic tooth implant is either fixed permanently by screws, wires or temporarily. In each case an abutement is attached to the implant fixture. Where the prosthetic crown bridge or denture is fixed to the abutement with either lag screws or cement. The prosthetic tooth implant is removable and a corresponding adapter is placed in the prosthetic so that two pieces are secured together.

The risks and complications related to the implant therapy are divided into those that occur during surgery (such as excessive bleeding or nerve injury), those that occur in the first six months (such as infection and failure to Osseo integrate) and those that occur long term (such as peri-implantitis and mechanical failure). In the presence of healthy tissues a well-integrated implant with appropriate biomechanical loads have a long-term success rates of 93 to 98 percent for the fixture and 10 to 15 years lifespan for the prosthetic teeth.

The dental implants have many disadvantages. The modern day new dental implants are costly. Another major drawback is that the dental implants require surgery. As the dental implant have to be placed in the jaw bone. The dental implant complication rate is about 1%, but an average is between 5-10%. Further the risks are infection, prolonged bleeding, damage to other teeth, nerve damage, delayed bone healing and jaw fracture.

The dental implant and the artificial teeth/tooth will probably have to be replaced someday i.e. the fixed implant bridge with plastic teeth will wear out and need to be replaced. A porcelain crown or bridge on an implant chip deteriorates. Implant teeth are more complex and costly than the surgery and bone grafting.

Over time there is bone loss after many years around dental implant. Further if too much bone is lost, the whole implant must be replaced. Also the original surgery and fabrication design of the teeth are a huge factor in the long-term health of the dental implant.

The most common disadvantage of the dental implants is that they take time for bone integration. The jaw bone heals slowly. Patient with bone grafting takes time from 3-18 months for jaw bone healing.

The tooth implants are permanently drilled and attached to the jaw bone. The drilling and fixation of the implant causes pain and permanent damage to the jaw bone. The damage to the jaw bone negatively impacts the ability to re-grow teeth, which is something that can be available in future. Further the metal implants tend to harbor and staff bacteria and cause infections. The conventional polymer implants denature and fail to maintain the true feel of natural teeth or gums. When conventional implants are subjected to trauma, the jaw may break as the implants are physically attached to the jaw.

Hence there is a need for a tooth implant configured to replace a missing tooth without damaging the dental cavities. Also there is a need for tooth implant, which houses the roots of teeth and is located beneath the gum line.

The above-mentioned shortcomings, disadvantages and problems are addressed herein and which will be understood by reading and studying the following specification.

OBJECTIVES OF THE EMBODIMENTS

The primary objective of the embodiment herein is to provide a synthetic polymer tooth for replacing a missing tooth.

Another object of the embodiment herein is to provide a composition for synthetic polymer tooth comprising a moldable polymer epoxy resin and weighted particulate additives.

Yet another object of the embodiment herein is to synthesize synthetic polymer tooth that has an exterior that is configured to bow out over a period of time, such that when the partially cured replacement is placed in a recipients dental cavity the replacement will lock into place while fully curing the dental cavity over a period of time.

Yet another object of the embodiment herein is to provide a synthetic polymer tooth replacement comprising the root system of a tooth, such that the root system of a tooth is configured to accept a crown thereon, creating a full tooth replacement.

Yet another object of the embodiment herein is to provide a synthetic polymer tooth made from hypoallergenic polymer epoxy resin.

Yet another object embodiment herein is to provide a synthetic polymer tooth, which is easily removable, when natural tooth replacement becomes available.

Yet another object of the embodiment herein is to provide a synthetic polymer tooth, which has the size and shape of the original missing tooth beneath the gum line.

Yet another object of the embodiment herein is to provide a synthetic polymer tooth which is accepted by the gum and leaving the gums in a healthy and uninjured state.

Yet another object of the embodiment herein is to provide synthetic polymer tooth replacement comprising a moldable polymer epoxy resin and weighted particulate additives.

Yet another object of the embodiment herein is to provide synthetic polymer tooth replacement for dental cavity, such that the replacement locks into the dental cavity while fully curing over a period of time.

Yet another object of the embodiment herein is to provide a method of tooth replacement which allows for Osseo integration of an implant lining made of titanium while having the ability to be dislodged by a dentist or in the event of impact trauma to the mandible or upper jaw, preventing bone trauma.

The embodiment herein will become readily apparent from the following detailed description taken in conjunction with the accompanying drawings.

SUMMARY

The various embodiments herein provide a synthetic polymer tooth replacement for replacing a missing tooth. The synthetic polymer tooth replacement is synthesized from a composition. The composition comprises a moldable resin and weighted particular additives. The polymer tooth replacement is synthesized by centrifuging the composition. Further the composition is poured in a mold. The mold is customized to a recipients missing tooth. The synthetic polymer tooth replacement has an exterior that is configured to bow out over a period of time. The synthetic polymer tooth replacement when placed in the recipient's dental cavity locks into the place and fully cures over a period of time.

According to one embodiment herein, the synthetic polymer tooth implant composition comprises of biological materials. The biological materials include an epoxy resin and synthetic polymer bio-materials. The synthetic polymer bio-materials are a 4-amino 7-phenyl pyrazol[3,4-d]pyrimidine (PP3) and a polypropylene (PP). The polypropylene is in a form of a mesh. The polypropylene provokes a scaring of a dental tissue. The polypropylene and the epoxy resin of the tooth implant get adhered to a tooth cavity by absorption.

According to one embodiment, a method of synthesizing synthetic polymer tooth implant, the method comprising the following steps of mixing a 4-amino 7 phenyl pyrazol [3,4-d]pyrimidine (PP3) with an epoxy resin. The next step is centrifuging a 4-amino 7 phenyl pyrazol[3,4-d]pyrimidine (PP3) with the epoxy resin to obtain a uniform mixture. The mixture is poured into a polypropylene mesh to obtain the tooth implant. The tooth implant comprises a root system of a tooth and the tooth implant is configured to accept a crown thereby creating a full tooth replacement. The tooth implant is a synthetic polymer replacement tooth.

According to one embodiment herein, the synthetic polymer tooth replacement is used as a tooth implant to replace a missing tooth. The synthetic polymer tooth replacement comprises a moldable resin composition i.e. polymer epoxy resin and weighted particulate additives. The additives include epoxy-activated particles. The synthetic polymer tooth replacement is configured to be accepted by or lock into the gums. The synthetic polymer tooth replacement comprises the root system of a tooth and is configured to accept a crown thereon, creating a full tooth replacement.

According to one embodiment herein, the synthetic polymer tooth replacement of the present invention is made using a hypoallergenic polymer epoxy resin. The synthetic polymer is a build of polypropylene mesh biomaterial (PP3), bound by thermoset epoxy polymer (as a resin), coated with polymer biomaterial (PP). The PP and PP3 are synthetic polymer biomaterials.

According to one embodiment herein, the synthetic polymer tooth comprises a prosthetic dentin unit and abutement. The crown is affixed on the abutement.

According to one embodiment herein, the biomaterial 4-amino-7-phenylpyrazol[3,4-d]pyrimidine (PP3) has a high level of absorption. The PP3 is added to a medical grade form of polypropylene mesh. The polypropylene mesh is coated with an additional exterior layer of polypropylene (PP). The PP has property of provoking the scaring of tissue. This property of PP is used, with which the jawbone lining of dental cavity will knit and the dentin cement naturally holds the dentin in place. The material becomes absorbent into the thermoset epoxy polymer while the cast mold is lined with it. The material will spread out for adhesion by way of absorption.

According to one embodiment herein, the first generation biomaterial for the synthesis of false dentin and abutement comprises of polypropylene mesh (PP) layered with the thermoset epoxy resin. The second generation biomaterial for the synthesis of false dentin and abutement comprises of biomaterial 4-amino-7-phenylpyrazol[3,4-d]pyrimidine (PP3) layered with epoxy resin. The final stage of the abutement synthesis comprises spray of medical grade acetone. Further the surface of false dentin and abutement is modified with a fine brushing dental tool.

According to one embodiment herein, the method of applying the artificial tooth for replacement of teeth comprises the following steps: assessing the state of the gums, existing bone and dentin cavities, by three dimensional computer graphics of x-rays. Further subjecting the jaw to CT scan by using software to render a cast mould using a 3D printer. The resins and the biological materials are mixed and centrifuged. Further the mixture of resin and biological materials is poured into the mould to get an implant.

According to one embodiment herein, the existing scar tissue, dentin and cement are surgically removed by a periodontist. Further the implant is then set into place and temporary tension fibers are pulled by a spool. The spool is screwed into the abutement to pull the false dentin polymer epoxy resin inward. The prosthetic dentin and abutement is then fitted with a plastic filament cap, and a metal filament wire is attached. The wire is having a breakaway tension tolerance of 20 pounds. The wire is connected to abutement spool. All the metal components such as the wire, is made of surgical grade steel. The spool and the wire lead the false dentin to grip for healing and setting to the cavity. The epoxy resin along with biological polymers, spool and filaments are heated after the apparatus is implanted. The epoxy polymer begins to cure. After one or two weeks, the biological tissue knits with PP, the spool and the filaments are then removed. Tissue damage occurring during heating process promotes scaring and promotes the knitting of the biological tissue with PP and epoxy resin bound PP3.

According to one embodiment herein, the synthetic polymer tooth replacement synthesized from polymer epoxy resin bows with exposure to a catalyst. The polymer epoxy resin is poured into a mold, resulting in a synthetic polymer tooth replacement that has a lower concentration of compounds that are reactive in the interior of the replacement than at the exterior. The mold is made in accordance with a computer-generated topography of the gum and jaw cavities. Because of this reason the mold and the synthetic polymer tooth match a recipient's missing natural teeth. The resin is easily moldable/flexible, hence the tooth replacement is easily inserted into a recipients gum cavity. The replacement is shaved to a nub. The nub is fitted with a custom crown, which is secured to the replacement without disturbing the dental cavities beneath the gum line and in the jaw bones. The replacement is easily removed when natural tooth replacement becomes available.

According to one embodiment herein, the synthetic polymer tooth replacement has a size and shape of the original missing tooth beneath the gum line. This increases the likelihood of the replacement being accepted by the gum while also leaving the gums in a healthy and uninjured state. The use of synthetic polymer tooth replacement of the present disclosure does not worsen trauma to the jaw. Further an external impact such as punch dislodges the implants just like the natural teeth.

According to one embodiment herein, the synthetic polymer tooth replacement is required to be placed either shortly after the natural tooth has fallen out or been taken out. Alternatively, if the dentin canals are treated and capped, the caps are later removed and the synthetic polymer tooth replacement is placed shortly thereafter. In some cases the synthetic polymer tooth replacement is not accepted by the gums unless the natural teeth are freshly extracted and the gums are not already healed and scarred over.

According to one embodiment herein, the successes of the implant depends on endodontic and periodontic surgical preparations, applications and follow up as in case of a standard root canal procedure. After implanting the synthetic polymer tooth replacement the follow up is necessary to avoid the risk of rejection as the implant is affixed with filaments and wires which substitute roots, where the spools and wires pierce the nerves associated with the jaw. The nerves associated with jaw and cavity determines the acceptance of the artificial dentin coated with PP and PP3.

According to one embodiment herein, after implantation by fusing with a coating of biomaterial, the polymer is cured and epoxy sets slowly, in the same manner by which ameloblast cells form dentin. The polymers and epoxy resin being a chain matrix hardens when introduced to the dental cavity and the increase of temperature delivered by metal filaments attached to the abutement.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
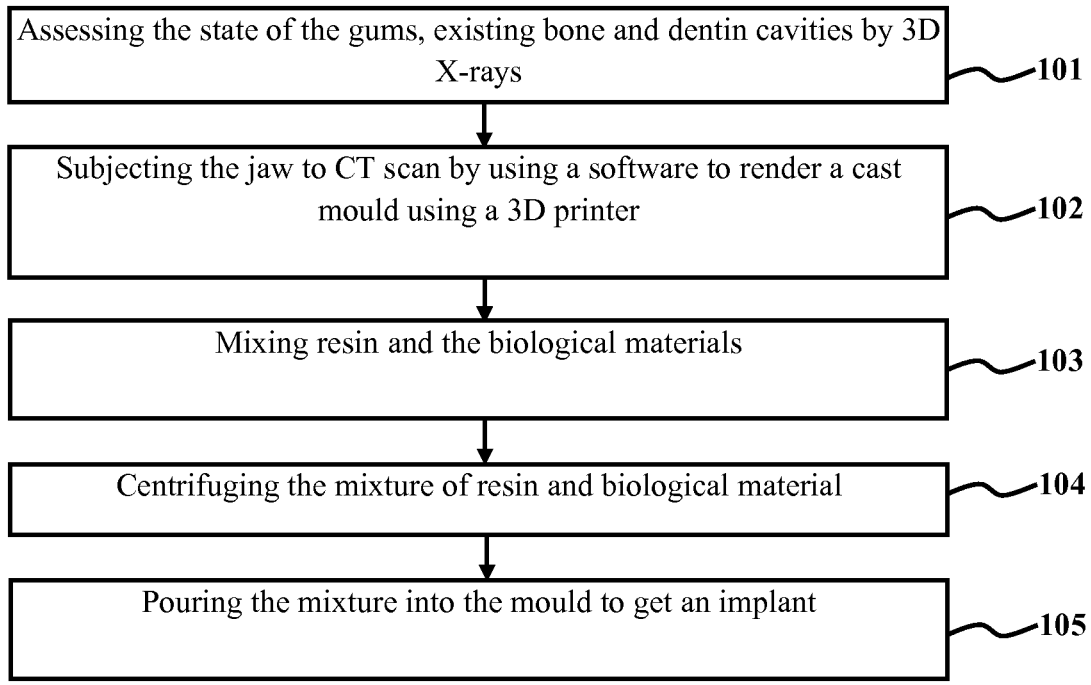
FIG. 1 illustrates a flowchart indicating a method for synthesizing the synthetic polymer tooth implant, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a synthetic polymer tooth replacement for replacing a missing tooth. The synthetic polymer tooth replacement is synthesized from a composition. The composition comprising a moldable resin and weighted particular additives. The polymer tooth replacement is synthesized by centrifuging the composition. Further the composition is poured in a mold. The mold is customized to a recipients missing tooth. The synthetic polymer tooth replacement has an exterior that is configured to bow out over a period of time. The synthetic polymer tooth replacement when placed in the recipient's dental cavity locks into the place and fully cures over a period of time.

According to one embodiment herein, the synthetic polymer tooth implant composition comprises of biological materials. The biological materials include an epoxy resin and synthetic polymer bio-materials. The synthetic polymer bio-materials are a 4-amino 7-phenyl pyrazol[3,4-d]pyrimidine (PP3) and a polypropylene (PP). The polypropylene is in a form of a mesh. The polypropylene provokes a scaring of a dental tissue. The polypropylene and the epoxy resin of the tooth implant get adhered to a tooth cavity by absorption.

According to one embodiment herein, a method of synthesizing synthetic polymer tooth implant, the method comprising the following steps: mixing a 4-amino 7 phenyl pyrazol[3,4-d]pyrimidine (PP3) with an epoxy resin. The next step is centrifuging a 4-amino 7 phenyl pyrazol[3,4-d]pyrimidine (PP3) with the epoxy resin to obtain a uniform mixture. The mixture is poured into a polypropylene mesh to obtain the tooth implant. The tooth implant comprises a root system of a tooth and wherein the tooth implant is configured to accept a crown thereby creating a full tooth replacement. The tooth implant is a synthetic polymer replacement tooth.

According to one embodiment herein, the synthetic polymer tooth replacement is used as a tooth implant to replace a missing tooth. The synthetic polymer tooth replacement comprises a moldable resin composition i.e. polymer epoxy resin and weighted particulate additives. The additives include an epoxy-activated particles. The synthetic polymer tooth replacement is configured to be accepted by or lock into the gums. The synthetic polymer tooth replacement comprises the root system of a tooth and is configured to accept a crown thereon, creating a full tooth replacement.

According to one embodiment herein, the synthetic polymer tooth replacement of the present invention is made using a hypoallergenic polymer epoxy resin. The synthetic polymer is a build of polypropylene mesh biomaterial (PP3), bound by a thermoset epoxy polymer (as a resin), coated with polymer biomaterial (PP). The PP and PP3 are synthetic polymer biomaterials.

According to one embodiment herein, the synthetic polymer tooth comprises a prosthetic dentin unit and abutement. The crown is affixed on the abutement.

According to one embodiment herein, the biomaterial 4-amino-7-phenylpyrazol[3,4-d]pyrimidine (PP3) has a high level of absorption. The PP3 is added to a medical grade form of polypropylene mesh. The polypropylene mesh is coated with an additional exterior layer of polypropylene (PP). The PP has property of provoking the scaring of tissue. This property of PP is used, with which the jawbone lining of dental cavity will knit and the dentin cement naturally holds the dentin in place. The material becomes absorbent into the thermoset epoxy polymer while the cast mold is lined with it. The material will spread out for adhesion by way of absorption.

According to one embodiment herein, the first generation biomaterial for the synthesis of false dentin and abutement comprises of polypropylene mesh (PP) layered with the thermoset epoxy resin. The second generation biomaterial for the synthesis of false dentin and abutement comprises of biomaterial 4-amino-7-phenylpyrazol[3,4-d]pyrimidine (PP3) layered with epoxy resin. The final stage of the abutement synthesis comprises spray of medical grade acetone. Further the surface of false dentin and abutement is modified with a fine brushing dental tool.

According to one embodiment herein, the method of applying the artificial tooth for replacement of teeth comprises the following steps: assessing the state of the gums, existing bone and dentin cavities, by three dimensional computer graphics of x-rays. Further subjecting the jaw to CT scan by using software to render a cast mould using a 3D printer. The resins and the biological materials are mixed and centrifuged. Further the mixture of resin and biological materials is poured into the mould to get an implant.

According to one embodiment herein, the existing scar tissue, dentin and cement are surgically removed by a periodontist. Further the implant is then set into place and temporary tension fibers are pulled by a spool. The spool is screwed into the abutement to pull the false dentin polymer epoxy resin inward. The prosthetic dentin and abutement is then fitted with a plastic filament cap, and a metal filament wire is attached. The wire is having a breakaway tension tolerance of 20 pounds. The wire is connected to abutement spool. All the metal components such as the wire, is made of surgical grade steel. The spool and the wire lead the false dentin to grip for healing and setting to the cavity. The epoxy resin along with biological polymers, spool and filaments are heated after the apparatus is implanted. The epoxy polymer begins to cure. After one or two weeks, the biological tissue knits with PP, the spool and the filaments are then removed. Tissue damage occurring during heating process promotes scaring and promotes the knitting of the biological tissue with PP and epoxy resin bound PP3.

According to one embodiment herein, the synthetic polymer tooth replacement synthesized from polymer epoxy resin bows with exposure to a catalyst. The polymer epoxy resin is poured into a mold, resulting in a synthetic polymer tooth replacement that has a lower concentration of compounds that are reactive in the interior of the replacement than at the exterior. The mold is made in accordance with a computer-generated topography of the gum and jaw cavities. Because of this reason the mold and the synthetic polymer tooth match a recipient's missing natural teeth. The resin is easily moldable/flexible, hence the tooth replacement is easily inserted into a recipients gum cavity. The replacement is shaved to a nub. The nub is fitted with a custom crown, which is secured to the replacement without disturbing the dental cavities beneath the gum line and in the jaw bones. The replacement is easily removed when natural tooth replacement becomes available.

According to one embodiment herein, the synthetic polymer tooth replacement has a size and shape of the original missing tooth beneath the gum line. This increases the likelihood of the replacement being accepted by the gum while also leaving the gums in a healthy and uninjured state. The use of synthetic polymer tooth replacement of the present disclosure does not worsen trauma to the jaw. Further an external impact such as punch dislodges the implants just like the natural teeth.

According to one embodiment herein, the synthetic polymer tooth replacement is required to be placed either shortly after the natural tooth has fallen out or been taken out. Alternatively, if the dentin canals are treated and capped, the caps are later removed and the synthetic polymer tooth replacement is placed shortly thereafter. In some cases the synthetic polymer tooth replacement is not accepted by the gums unless the natural teeth are freshly extracted and the gums are not already healed and scarred over.

According to one embodiment herein, the successes of the implant depends on endodontic and periodontic surgical preparations, applications and follow up as in case of a standard root canal procedure. After implanting the synthetic polymer tooth replacement the follow up is necessary to avoid the risk of rejection as the implant is affixed with filaments and wires which substitute roots, where the spools and wires pierce the nerves associated with the jaw. The nerves associated with jaw and cavity determines the acceptance of the artificial dentin coated with PP and PP3.

According to one embodiment herein, after implantation by fusing with a coating of biomaterial, the polymer is cured and epoxy sets slowly, in the same manner by which ameloblast cells form dentin. The polymers and epoxy resin being a chain matrix hardens when introduced to the dental cavity and the increase of temperature delivered by metal filaments attached to the abutement.

Experimental Details

Materials and Methods

The synthetic polymer is a build of polypropylene mesh biomaterial 4-amino-7-phenylpyrazol[3,4-d]pyrimidine (PP3), bound by thermoset epoxy polymer (as a resin), coated with polymer biomaterial polypropylene (PP). PP and PP3 are synthetic polymer biomaterials. These embodiments comprise a prosthetic dentin unit and abutement to which a crown is affixed. As an embodiment, the thermoset epoxy polymer is a prior art, bearing specifications and references as follows:

Resinlab® EP1330LV Heat Cure Epoxy Polymer System Categories: Polymer; Adhesive; Thermoset; Epoxy; Epoxy Adhesive. The Resinlab™ EP1330 and EP1330LV are one part heat cure epoxy polymer systems. These polymers are also used as a small mass potting or staking compounds, or a dental dam adhesive and "dam and fill" applications, or general polymer systems. When the application requires high thermal conductivity, low shrinkage, low CTE and excellent adhesion to a wide variety of plastics, metals and circuit board materials these materials are used. EP1330 is a thixotropic adhesive; EP1330LV is semi-free flowing material which self levels, but still maintain a conformal build on circuit board components.

For the synthesis of the synthetic polymer tooth implant 4-amino-7-phenylpyrazol[3,4-d]pyrimidine (PP3) is added to a medical grade form of polypropylene mesh, coated with an additional exterior layer of polypropylene (PP). The PP3 has a high level of absorption. The synthetic polymer tooth implant initiates the scaring of tissue, with which the lining of the jawbone's dental cavity will knit. The knitting of synthetic polymer tooth implant is in lieu with that of the dentin cement that naturally holds the original dentin in place. The PP3 and PP material becomes absorbent into the thermoset epoxy polymer while the cast mold is lined with it. Further it is malleable and turns at high centrifugal force, to spread out for adhesion by way of absorption.

FIG. 1 illustrates a flowchart indicating a method for synthesizing the synthetic polymer tooth implant, according to an embodiment herein. The first step is assessing the state of the gums, existing bone and dental cavities by a 3D X rays (101). Further subjecting the jaw to CT scan by using software to render a cast mould using a 3D printer (102). The next step is mixing the resin and the biological materials (103). The biological materials are epoxy resin, 4-amino-7-phenylpyrazol[3,4-d]pyrimidine (PP3) and polypropylene (PP). Centrifuging the mixture of epoxy resin and the PP3 and PP (104). After centrifugation the mixture is poured into the mould to get an implant (105).

Figure 2:
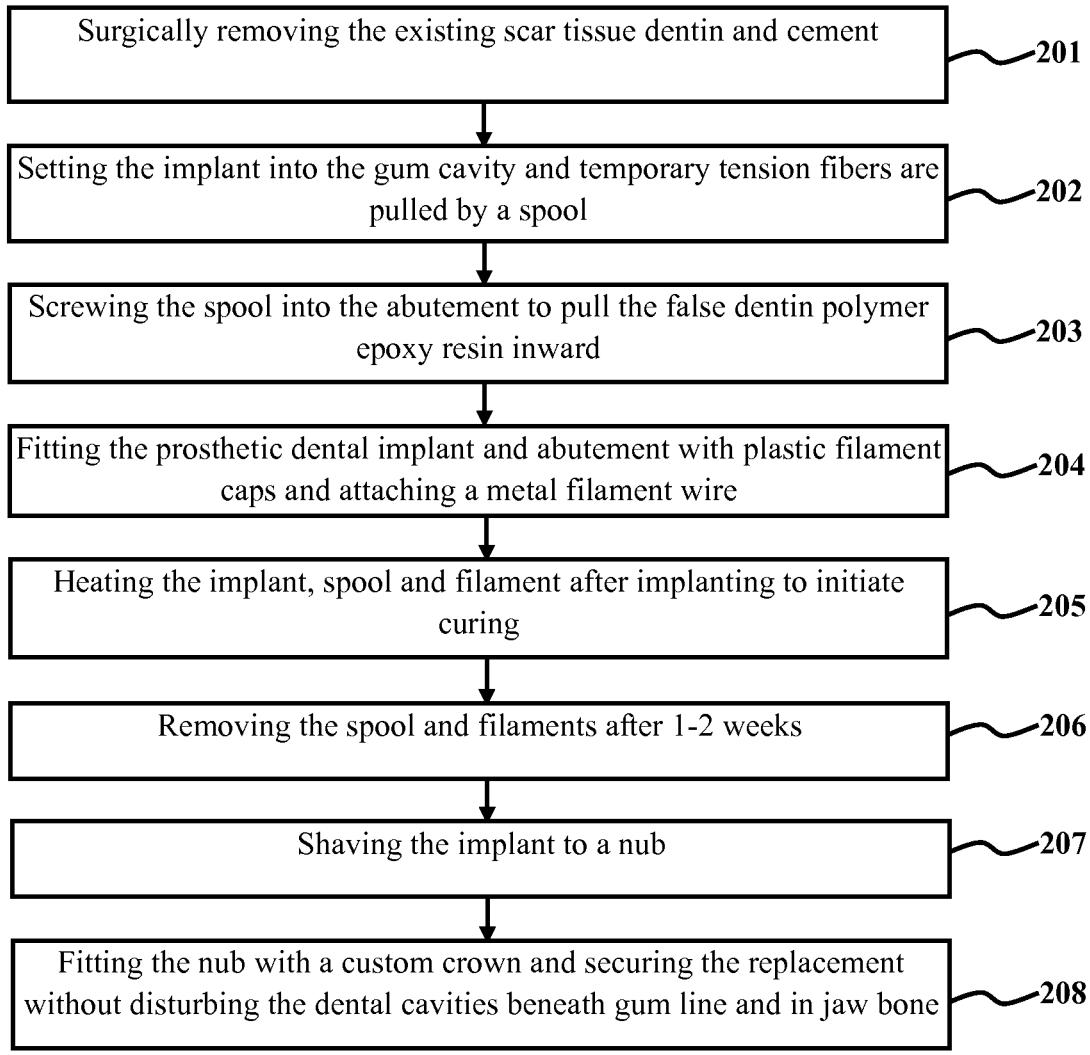
FIG. 2 illustrates a flowchart indicating a method of fixing/placing the synthetic polymer tooth implant in the gum cavity, according to an embodiment herein.

FIG. 2 illustrates a flowchart indicating a method of fixing/placing the synthetic polymer tooth implant in the gum cavity, according to an embodiment herein. The existing scar tissue, dentin and cement are surgically removed (201). The implant is set into the gum cavity and temporary tension fibers are pulled by a spool (202). The spool is screwed in to the abutements to pull the false dentin polymer epoxy resin inward (203). The prosthetic dental implant and the abutement is fitted with plastic filament caps and attaching a metal filament wire (204). The implant, spool and filaments are heated after implanting to initiate the curing (205). The spool and the filaments are removed after 1-2 weeks (206). The implant is shaved to a nub (207). The nub is fitted with a custom crown and secured with the replacement without disturbing the dental cavities beneath gum line and in jaw bone (208).

The state of the gums and existing bone and dentin cavities are assessed, by a three dimensional renderings of x-rays cross-referenced with CT scans of the jaw by software. A mould is prepared using a 3D printer.

The cast mold is then lined with a layer of Polypropylene mesh (PP) and an inner layer of PP3, which absorb the polymer epoxy resin.

The prosthetic dentin and abutement is then fitted with the plastic filament caps. The metal filament wires are attached to plastic filament caps, having a break-away tension tolerance of approximately 20 pounds, and connected to the abutement spool. All metal components are surgical grade steel and temporary.

Figure 3:
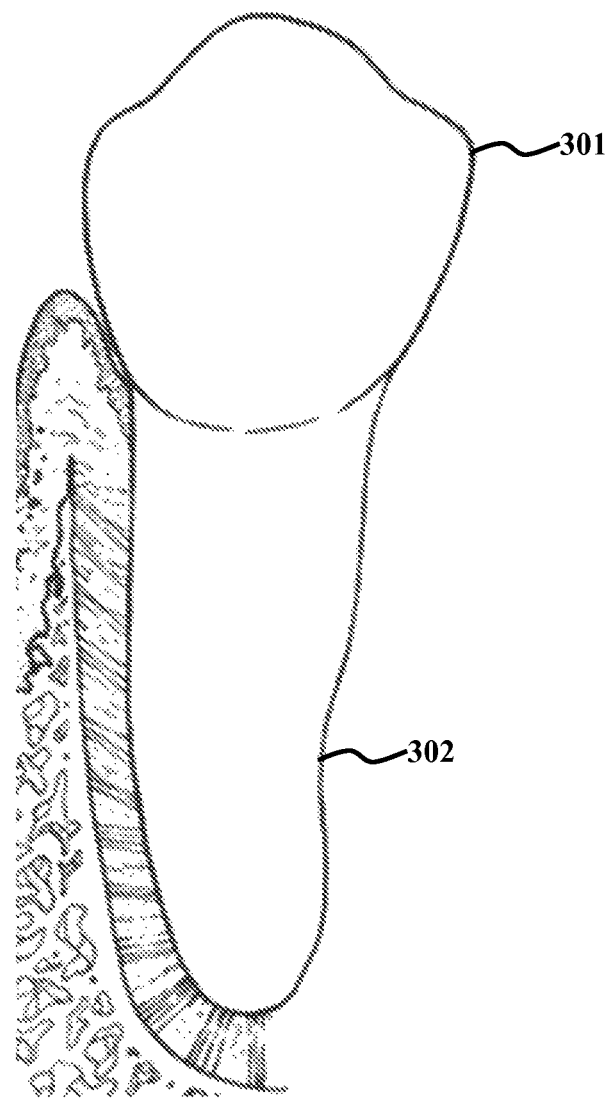
FIG. 3 illustrates a diagram showing the synthetic polymer tooth implant with affixed crown, according to an embodiment herein.

FIG. 3 illustrates a diagram showing the synthetic polymer tooth implant with affixed crown, according to an embodiment herein. Assessing the state of the gums, existing bone and dentin cavities, by three-dimensional renderings of X-rays. Further subjecting the jaw to CT scan by using software to render a cast mould using a 3D printer. The resins and the biological materials are mixed and centrifuged. The cast mold is then lined with a layer of Polypropylene Mesh (PP) and an inner layer of PP3, which absorb the polymer epoxy resin. The synthetic polymer tooth replacement comprises the root system or dental implant (302) of a tooth and is configured to accept a crown (301) thereon, creating a full tooth replacement.

Figure 4:
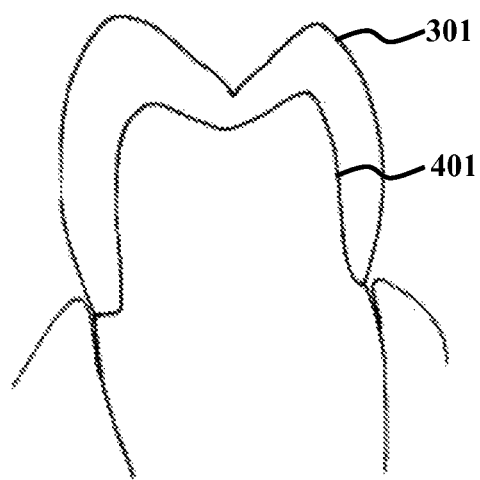
FIG. 4 illustrates a diagram showing the nub and the crown of the synthetic polymer tooth implant, according to an embodiment herein.

FIG. 4 illustrates a diagram showing the nub and the crown of the synthetic polymer tooth implant, according to an embodiment herein.

The resin is easily moldable/flexible, this makes the synthetic polymer tooth implant easily insertable into a recipients gum cavity. The replacement is shaved to a nub 401. The nub is fitted with a custom crown 301, which is secured to the replacement without disturbing the dental cavities beneath the gum line and in the jaw bones. The replacement is easily removed when natural tooth replacement becomes available. The synthetic polymer tooth replacement has a size and shape of the original missing tooth beneath the gum line. This increases the likelihood of the tooth replacement for acceptance by the gum. Also leaving the gums in a healthy and uninjured state. The use of synthetic polymer tooth replacement of the present disclosure does not worsen trauma to the jaw. Further an external impact such as punch dislodges the implants just like the natural teeth.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments, which as a matter of language might be said to fall there between.

What is claimed is:

1. A method of synthesizing synthetic polymer tooth implant, the method comprising steps of:
    mixing a 4-amino 7 phenyl pyrazol[3,4-d]pyrimidine (PP3) with an epoxy resin;

centrifuging a 4-amino 7 phenyl pyrazol[3,4-d]pyrimidine (PP3) with the epoxy resin to obtain an uniform mixture; and pouring the mixture into a polypropylene mesh to obtain the tooth implant.

2. The method according to claim 1, wherein the tooth implant comprises a root system of a tooth and wherein the tooth implant is configured to accept a crown thereby creating a full tooth replacement.

3. The method according to claim 1, wherein the tooth implant is a synthetic polymer replacement tooth.

* * * * *